United States Patent
Sallares et al.

(10) Patent No.: US 8,106,202 B2
(45) Date of Patent: Jan. 31, 2012

(54) METHOD FOR MAKING 1-SUBSTITUTED 1H-IMIDAZO [4,5-C] QUINOLIN-4-AMINE COMPOUNDS AND INTERMEDIATES THEREFOR

(75) Inventors: Juan Sallares, Barcelona (ES); Inés Petschen, Barcelona (ES); Francesc-Xavier Camps, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 1053 days.

(21) Appl. No.: 11/886,726

(22) PCT Filed: Mar. 20, 2006

(86) PCT No.: PCT/EP2006/060887
§ 371 (c)(1), (2), (4) Date: Jan. 14, 2008

(87) PCT Pub. No.: WO2006/100226
PCT Pub. Date: Sep. 28, 2006

(65) Prior Publication Data
US 2009/0005566 A1    Jan. 1, 2009

(30) Foreign Application Priority Data
Mar. 21, 2005  (EP) .................................. 05102229

(51) Int. Cl.
*C07D 471/04* (2006.01)
(52) U.S. Cl. ......................................................... 546/82
(58) Field of Classification Search .................... 546/82
See application file for complete search history.

(56) References Cited

U.S. PATENT DOCUMENTS

| 4,689,338 A | | 8/1987 | Gerster | |
|---|---|---|---|---|
| 5,741,908 A | * | 4/1998 | Gerster et al. | 546/81 |
| 7,323,568 B2 | * | 1/2008 | Naddaka et al. | 546/82 |

OTHER PUBLICATIONS

Izumi T. et al., Bioorganic & Medicinal Chemistry, vol. 11, 2003, pp. 2541-2550.
Vercek B et al., Journal of Organic Chemistry, American Chemical Society, vol. 44, No. 10, 1979, pp. 1695-1699.

* cited by examiner

*Primary Examiner* — Susannah Chung
(74) *Attorney, Agent, or Firm* — Birch, Stewart, Kolasch & Birch, LLP

(57) ABSTRACT

The present invention concerns a method for manufacturing 1-substituted 1H-imidazo[4,5-c]quinolin-4-amine compounds through their corresponding formamides. The invention also concerns new formamide intermediates.

18 Claims, No Drawings

METHOD FOR MAKING 1-SUBSTITUTED 1H-IMIDAZO [4,5-C] QUINOLIN-4-AMINE COMPOUNDS AND INTERMEDIATES THEREFOR

TECHNICAL FIELD

The present invention concerns a method for manufacturing 1-substituted 1H-imidazo[4,5-c]quinolin-4-amine compounds, particularly 1-isobutyl-1H-imidazo[4,5-c]quinolin-4-amine, through their corresponding formamides. The invention also concerns new formamide intermediates.

BACKGROUND OF THE INVENTION

Imiquimod, 1-isobutyl-1H-imidazo[4,5]quinolin-4-amine, is an immune response modifier, useful for treating viral infections, such as genital warts.

Imiquimod was firstly disclosed in EP 145340 and has the following structural formula:

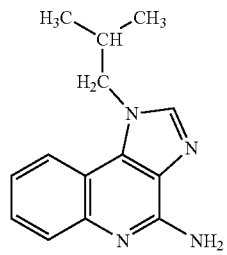

Some different methods have been disclosed for the preparation of imiquimod and other 1-substituted-1H-imidazo[4,5-c]quinolin-4-amines. Certain methods, such as those disclosed in U.S. Pat. No. 4,988,815, U.S. Pat. No. 5,578,727, U.S. Pat. No. 5,602,256, U.S. Pat. No. 4,698,348, U.S. Pat. No. 4,689,338 and U.S. Pat. No. 4,929,624, use the corresponding 4-chloro precursors and their conversion to 4-amino final products implies very energetic conditions comprising heating under pressure in the presence of ammonium hydroxide or ammonia in hermetically sealed reactors for long periods of time. Such required pressures are extremely high, thus forcing to use special manufacturing facilities. Moreover, said processes afford 4-amino final products with moderate yields.

The present invention provides a method for manufacturing a compound of formula (I):

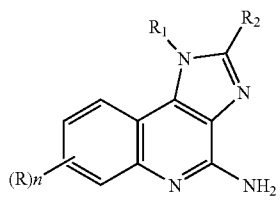

wherein
$R_1$ is selected from the group consisting of straight-chain or branched-chain alkyl containing one to ten carbon atoms and substituted straight-chain or branched-chain alkyl containing one to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; straight-chain or branched-chain alkenyl containing two to ten carbon atoms and substituted straight-chain or branched-chain alkenyl containing two to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

$R_2$ is selected from the group consisting of hydrogen; straight-chain or branched-chain alkyl containing one to eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

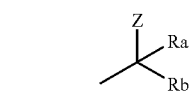

wherein $R_a$ and $R_b$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and Z is selected from the group consisting of alkoxy containing one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, and thioalkyl of one to four carbon atoms;

R is selected from the group consisting of lower alkoxy, halogen, and lower alkyl;

and n is zero or one, or a pharmaceutically acid addition salt thereof.

The present invention shows important advantages over the prior art because high-pressure conditions are not required to conduct the transformation at gentle reaction temperature conditions, thus enabling to perform the process in conventional facilities. Contrary to prior art, reaction times are short and compounds (I) can be isolated almost quantitatively.

The present invention comprises:

(i) Reacting a 4-halo-1H-imidazo[4,5]quinoline (II):

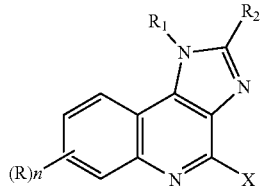
(II)

wherein R, $R_1$, $R_2$ and n are as defined above, and X is a halogen selected from the group consisting of chlorine and bromine, with formamide, thus providing the compound of formula (III):

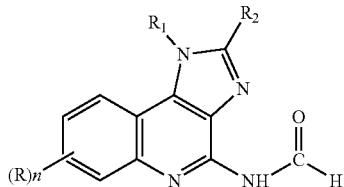
(III)

wherein R, $R_1$, $R_2$ and n are as defined above, and (ii) Converting (III) to final compound (I) by thermal treatment or by acid or basic hydrolysis.

The intermediates of general formula (II) wherein X is chlorine can be obtained by known methods, such as those disclosed in U.S. Pat. No. 4,988,815, U.S. Pat. No. 5,578,727, U.S. Pat. No. 5,602,256, U.S. Pat. No. 4,698,348, U.S. Pat. No. 4,689,338 and U.S. Pat. No. 4,929,624. When X is bromine, intermediates of general formula (II) can be prepared, for instance, from the corresponding N-oxides by reaction with phosphorus oxybromide.

According to the present invention, 1-substituted 1H-imidazo[4,5-c]quinolin-4-amines of general formula (I) can be prepared as shown in Scheme 1:

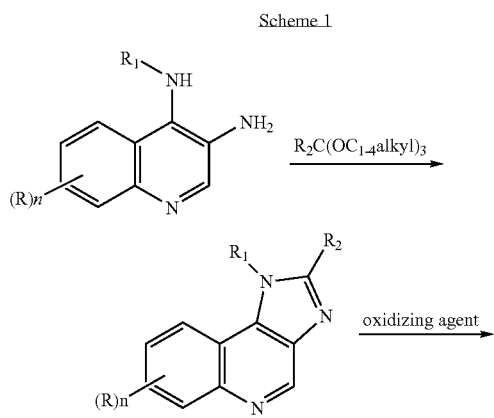

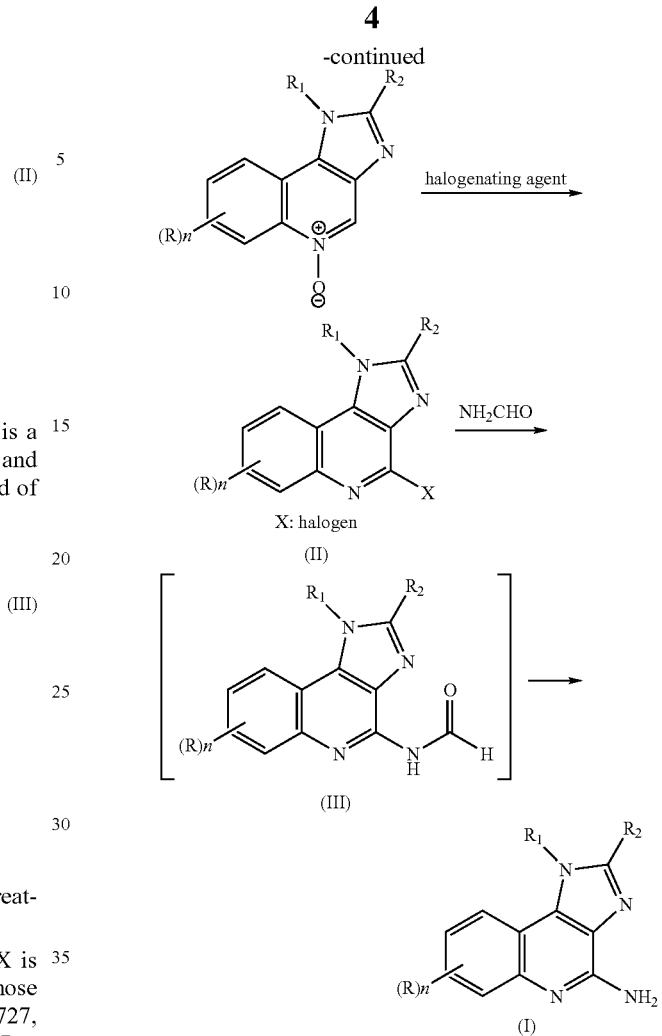

In another embodiment, the 1-substituted 1H-imidazo[4,5-c]quinoline-4-formamide (III) intermediates are prepared by reacting 4-halo-1H-imidazo[4,5-c]quinolines (II) with formamide in solvolytic conditions or with formamide in another solvent medium, in the presence of a base, in a wide range of temperatures, preferably from about 25 to about 150° C., and more preferably from about 70 to about 110° C.

In another embodiment, said solvent medium can be selected from the group of aprotic polar solvents such as dimethylsulfoxide, dimethylacetamide, N-methylpiperidone, N-methylpyrrolidone, dimethylformamide and 1,3-dimethyl-2-imidazolidinone, or mixtures thereof, preferably dimethylsulfoxide.

In another embodiment, when aprotic polar solvents are used, addition of a phase-transfer catalyst is optional. The phase-transfer catalyst is selected from the group consisting of tetrabutylammonium bromide, tetrabutylammonium chloride and tetrabutylammonium hydrogen sulfate. Tetrabutylammonium chloride and tetrabutylammonium hydrogen sulfate are preferred.

In another embodiment, the bases are selected from the group consisting of alkaline or alkaline earth metal hydroxydes, alkaline or alkaline earth metal carbonates, alkaline or alkaline earth metal bicarbonates, alkaline or alkaline earth metal alkoxides or alkaline or alkaline earth metal hydrides. Alkoxides and more specifically potassium tert-butoxide are preferred.

Intermediate formamides (III) can be isolated from the reaction medium or alternatively it is possible to force their complete conversion to corresponding final compounds (I). When compounds (III) are isolated, then they can be hydrolyzed by known methods of Organic Chemistry. The inventors have preferred not to isolate said intermediates in order to simplify the process.

In another embodiment, intermediate formamides (III) are not isolated.

In another embodiment, the present invention comprises the compounds of formula (III).

In a more preferred embodiment, the present invention comprises the compound of formula (III) which is 1-isobutyl-1H-imidazo[4,5-c]quinoline-4-formamide.

Advantageously, the method of the present invention does not require special manufacturing facilities because high pressure is not required and operation temperatures are gentle. Moreover, when the intermediate formamides are not isolated, the final corresponding products are afforded in a unique step with an almost quantitative yield.

The various aspects of the present invention are described more in details in the non-limitative examples presented hereinafter.

EXAMPLE 1

1-isobutyl-1H-imidazo[4,5-c]quinoline-4-formamide

Potassium tert-butoxide (4.32 g, 0.038 mole), 4.5 mL of dimethylacetamide and 1.53 mL (0.038 mole) of formamide were added in a 50-mL round-bottomed flask, under inert atmosphere followed by stirring for 30 minutes. After addition of 4-chloro-1H-imidazo[4,5-c]quinoline (1 g, 3.8 mmoles), the mixture was heated at 120° C., followed by stirring for 1 hour and then cooled to room temperature. The reaction mixture was filtered followed by washing with abundant water and dried to give 0.4 g of 1-isobutyl-1H-imidazo[4,5-c]quinolin-4-amine. Yield 39%.

The mother waters were concentrated under vacuum and precipitated with methylene dichloride to give 0.5 g of 1-isobutyl-1H-imidazo[4,5-c]quinoline-4-formamide. Yield 54%.

Mp 225-226° C.

IR: 3469, 3177, 3127, 2954, 1687, 1582 cm$^{-1}$.

$^1$HNMR (CDCl$_3$): 9.98 (d, J=10.4 Hz, 1H, CHO), 9.66 (d, J=10.8 Hz, 1H, NH), 8.13 (s, 1H, NCH=N), 8.04 (m, 2H, aromatic), 7.64 (m, 1H, aromatic), 7.52 (m, 1H, aromatic), 4.36 (d, J=7.2 Hz, 2H, CH$_2$), 2.37 (m, 1H, (CH$_3$)$_2$CH), 1.05 (d, J=6.8 Hz, 6H, 2CH$_3$).

$^{13}$CRMN (CDCl$_3$): 162.8 (CO), 144.27 (NCHN), 143.86 (NCNH), 133.98 (C ar), 129.25 (CH ar), 128.22 (CH ar), 127.83 (CH ar), 124.87 (CH ar), 120.03 (CH ar), 116.82 (Car), 109.97 (CH ar), 55.19 (CH$_2$), 28.81 ((CH$_3$)$_2$CH), 19.78 (CH$_3$).

EXAMPLE 2

1-isobutyl-1H-imidazo[4,5-c]quinolin-4-amine

Potassium tert-butoxide (2.16 g, 0.019 mole), 4.5 mL of dimethylsulfoxide and 0.76 mL (0.019 mole) of formamide were added in a 50-mL round-bottomed flask, under inert atmosphere followed by stirring for 30 minutes. After addition of 4-chloro-1H-imidazo[4,5-c]quinoline (1 g, 3.8 mmoles), the mixture was heated at 105° C., followed by stirring for 2 hours and then cooled to room temperature.

Then 10 mL of water and 6N HCl were sequentially added until pH 8. The reaction mixture was filtered followed by washing with abundant water and dried to give 0.91 g of 1-isobutyl-1H-imidazo[4,5-c]quinolin-4-amine. Yield 98%.

EXAMPLE 3

1-isobutyl-1H-imidazo[4,5-c]quinolin-4-amine

Potassium tert-butoxide (3.69 g, 0.033 mole), 5 mL of dimethylacetamide and 1.31 mL (0.033 mole) of formamide were added in a 50 mL round-bottomed flask, under inert atmosphere followed by stirring for 30 minutes. After addition of 4-bromo-1H-imidazo[4,5-c]quinoline (1 g, 3.3 mmoles), the mixture was heated at 140° C., followed by stirring for 2 hours and then cooled to room temperature. Then 10 mL of water were added and the reaction mixture was filtered followed by washing with abundant water and dried to give 0.75 g of 1-isobutyl-1H-imidazo[4,5-c]quinolin-4-amine. Yield 75.4%.

The invention claimed is:

1. A process for manufacturing 1H-imidazo[4,5-c]quinolin-4-amine of formula (I):

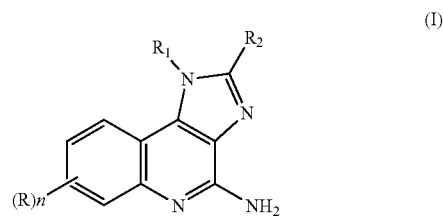

wherein $R_1$ is selected from the group consisting of straight-chain or branched-chain alkyl containing one to ten carbon atoms and substituted straight-chain or branched-chain alkyl containing one to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; straight-chain or branched-chain alkenyl containing two to about ten carbon atoms and substituted straight-chain or branched-chain alkenyl containing two to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

R₂ is selected from the group consisting of hydrogen; straight-chain or branched-chain alkyl containing one to eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

wherein R$_a$ and R$_b$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and Z is selected from the group consisting of alkoxy containing one to four carbon atoms, alkylamido wherein the alkyl group contains one to four carbon atoms, amino, substituted amino wherein the substituent is alkyl or hydroxyalkyl of one to four carbon atoms, azido, chloro, hydroxy, 1-morpholino, 1-pyrrolidino, and thioalkyl of one to four carbon atoms; R is selected from the group consisting of lower alkoxy, halogen, and lower alkyl; and n is zero or one, that comprises i. reacting a 4-halo-1H-imidazo[4,5]quinoline of formula (II):

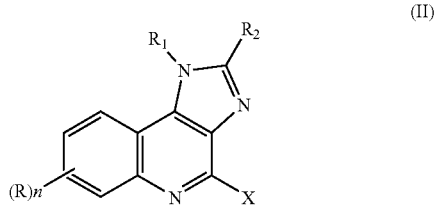

wherein R, R₁, R₂ and n are as defined above; and X is a halogen selected from the group consisting of chlorine and bromine, with formamide, thus obtaining 1H-imidazo[4,5]quinolin-4-formamide of formula (III):

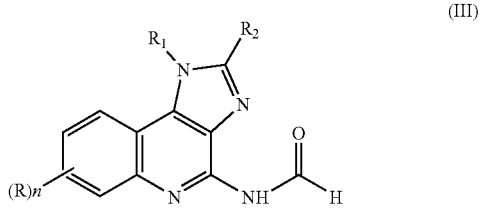

wherein R, R₁, R₂ and n are as defined above; and
ii. removing the formyl group of compound (III).

2. The process according to claim 1, wherein the formamide is under solvolytic conditions or forms a mixture with another solvent, in the presence of a base.

3. The process according to claim 2, wherein the solvent is an aprotic polar solvent.

4. The process according to claim 3, wherein the aprotic polar solvent is selected from the group consisting of dimethylsulfoxide, dimethylacetamide, N-methylpiperidone, N-methylpyrrolidone, dimethylformamide and 1,3-dimethyl-2-imidazolidinone, or mixtures thereof.

5. The process according to claim 4, wherein the solvent is dimethylsulfoxide.

6. The process according to claim 2, wherein the base is selected from the group consisting of alkaline or alkaline earth metal hydroxides, alkaline or alkaline earth metal carbonates, alkaline or alkaline earth metal bicarbonates, alkaline or alkaline earth metal alkoxides and alkaline or alkaline earth metal hydrides.

7. The process according to claim 6, wherein the base is an alkaline alkoxide or alkaline earth metal alkoxide.

8. The process according to claim 7, wherein the base is an alkaline alkoxide.

9. The process according to claim 8, wherein the alkaline alkoxide is potassium tert-butoxide.

10. The process according to claim 2, which comprises the optional use of a phase-transfer catalyst when another solvent is used.

11. The process according to claim 10, wherein said phase-transfer catalyst is selected from the group consisting of tetrabutylammonium bromide, tetrabutylammonium chloride and tetrabutylammonium hydrogen sulfate.

12. The process according to claim 11, wherein said phase-transfer catalyst is tetrabutylammonium chloride or tetrabutylammonium hydrogen sulfate.

13. The process according to claim 1, wherein removing said formyl group is performed by a method selected from the group consisting of: a) thermal treatment; b) acid hydrolysis; and, c) basic hydrolysis.

14. The process according to claim 1, wherein the intermediate formamide (III) is not isolated.

15. The process according to claim 1, wherein the temperature is in the range from about 25 to about 150° C.

16. The process according to claim 15, wherein the temperature is in the range from about 70 to about 110° C.

17. A compound of formula (III)

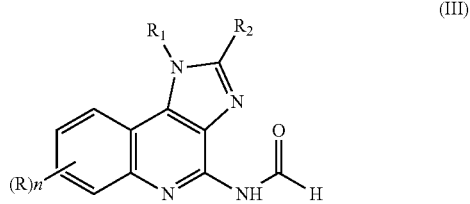

wherein
R₁ is selected from the group consisting of straight-chain or branched-chain alkyl containing one to ten carbon atoms and substituted straight-chain or branched-chain alkyl containing one to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; straight-chain or branched-chain alkenyl containing two to about ten carbon atoms and substituted straight-chain or branched-chain alkenyl containing two to ten carbon atoms, wherein the substituent is selected from the group consisting of cycloalkyl containing three to six carbon atoms and cycloalkyl containing three to six carbon atoms substituted by straight-chain or branched-chain alkyl containing one to four carbon atoms; hydroxyalkyl of one to six carbon atoms; alkoxyalkyl wherein the alkoxy moiety contains one to four carbon atoms and the alkyl moiety contains one to six carbon atoms; acyloxyalkyl wherein the acyloxy moiety is alkanoyloxy of two to four carbon atoms or benzoyloxy, and the alkyl moiety contains one to six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to four carbon atoms, alkoxy of one to four carbon atoms, and halogen, with the proviso that when said benzene ring is substituted by two of said moieties, then the moieties together contain no more than six carbon atoms;

$R_2$ is selected from the group consisting of hydrogen; straight-chain or branched-chain alkyl containing one to eight carbon atoms; benzyl; (phenyl)ethyl; and phenyl; the benzyl, (phenyl)ethyl, or phenyl substituent being optionally substituted on the benzene ring by one or two moieties independently selected from the group consisting of lower alkyl, lower alkoxy, halogen, and

wherein $R_a$ and $R_b$ are independently selected from the group consisting of hydrogen, alkyl of one to four carbon atoms, phenyl, and substituted phenyl wherein the substituent is selected from the group consisting of alkyl of one to four carbon atoms, alkoxy of one to four carbon atoms, and halogen; and Z is selected from the group consisting of alkoxy containing one to four carbon atoms, alkylamido wherein the alkyl group contains one to four carbon atoms, amino, substituted amino wherein the substituent is alkyl or hydroxyalkyl of one to four carbon atoms; azido, chloro, hydroxy, 1-morpholino, 1-pyrrolidino, and thioalkyl of one to four carbon atoms;

R is selected from the group consisting of lower alkoxy, halogen, and lower alkyl;

and n is zero or one.

18. A compound of formula (III) according to claim 17, which is 1-isobutyl-1H-imidazo[4,5-c]quinoline-4-formamide.

* * * * *